United States Patent [19]

Fischer

[11] Patent Number: 4,895,517
[45] Date of Patent: Jan. 23, 1990

[54] METHODS FOR PERFORMING VITAL DENTAL PULPOTOMY

[75] Inventor: Dan E. Fischer, Sandy, Utah

[73] Assignee: Ultradent Products, Inc., Salt Lake City, Utah

[21] Appl. No.: 38,198

[22] Filed: Apr. 14, 1987

[51] Int. Cl.$^4$ .............................................. A61C 5/02
[52] U.S. Cl. ...................................................... 433/224
[58] Field of Search ................. 433/224, 223; 424/147

[56] References Cited

U.S. PATENT DOCUMENTS

| | | | |
|---|---|---|---|
| 459,738 | 9/1891 | Black | 424/147 |
| 2,209,454 | 12/1938 | Guest | 424/147 |
| 2,322,735 | 8/1939 | Molnar | 424/147 |
| 2,584,082 | 4/1948 | MacAluso | 424/147 |
| 3,434,209 | 3/1969 | Weissman | 433/225 |
| 3,968,567 | 7/1976 | Nevins | 433/224 |
| 4,207,306 | 6/1980 | Jarcho | 423/598 |
| 4,251,565 | 2/1981 | Bowen | 433/226 |
| 4,382,792 | 5/1983 | Smith et al. | 433/217.1 |
| 4,522,593 | 6/1985 | Fischer | 433/136 |
| 4,548,583 | 10/1985 | Smith et al. | 433/228.1 |
| 4,551,100 | 11/1985 | Fischer | 433/218 |
| 4,578,055 | 3/1986 | Fischer | 604/2 |
| 4,597,960 | 7/1986 | Cohen | 424/147 |
| 4,659,751 | 4/1987 | Bowen | 433/228.1 |

OTHER PUBLICATIONS

Sipes et al., "The Use of Formocresol in Dentistry: A Review of the Literature," 17 Quintessence International, 416-417 (1986).
Myers et al., "Tissue Changes Induced by the Absorption of Formocresol from Pulpotomy Sites in Dogs," 5 Pediatric Dentistry, 6-8 (1983).
Lewis et al., "Formaldehyde in Dentistry: A Review of Mutagenic and Carcinogenic Potential," 103 Journal of the American Dental Association, 429-34 (Sep. 1981).
Messer et al., "Long Term Effects on Primary Molar Pulpotomies on Succedaneous Bicuspids," 59 Journal of Dental Research, 116-23 (Feb. 1980).
Pashley et al., "Systemic Distribution of $^{14}$C-Formaldehyde from Formocresol-Treated Pulpotomy Sites," 59 Journal of Dental Research, 602-07 (Mar. 1980).
Majare et al., "Short-Term Reactions of Human Dental Pulp to Formocresol and Its Components-A Clinical--Experimental Study," 87 Scandinavian Journal of Dental Research, 331-45 (1979).
Lazzari et al., "Biochemical Effects of Formocresol on Bovine Pulp Tissue," 45 Oral Surgery, 802 (May, 1978).
Myers et al., "Distribution of $^{14}$C-Formaldehyde After Pulpotomy With Formocresol," 96 Journal of the American Dental Association, 805-813 (May, 1978).
Makkes et al., "Reactions of the Living Organism to Dead and Fixed Dead Tissue," 4 Journal of Endodontics, 17-21 (Jan. 1978).

(List continued on next page.)

Primary Examiner—John J. Wilson
Attorney, Agent, or Firm—Workman, Nydegger & Jensen

[57] ABSTRACT

A method for repairing a tooth through the partial amputation of the coronal pulp at the orifices of the pulp canals, the arresting of hemorrhaging from the exposed cut ends of the pulpal tissue, and the fixing of those exposed cut ends by applying thereto a composition containing ferric ions, such as ferric sulfate and ferric subsulfate. The preferred composition can also be used for arresting hemorrhaging from the exposed cut ends of the pulpal tissue left in the pulp canals, in which case bleeding control and tissue fixation can be implemented simultaneously. The preferable use of a syringe-type controlled diffusion medicament applicator to infuse the preferred composition into tissue at the exposed cut ends of the pulpal tissue is also disclosed. Following tissue fixation, the barrier regions of fixed tissue between the empty coronal pulp chamber and vital pulp tissue remaining in the pulp canals are sealed from the coronal pulp chamber using a cement base, and the original tooth profile is restored, either by filling or capping.

51 Claims, 2 Drawing Sheets

OTHER PUBLICATIONS

Pruhs et al., "Relationship Between Formocresol Pulpotomies on Primary Teeth and Enamel Defects on Their Permanent Successors," 94 Journal of the American Dental Association, 698–700 (Apr. 1977).

Loos et al., "An Enzyme Histochemical Study of the Effect of Various Concentrations on Formocresol on Connective Tissues," 31 Oral Surgery, 571–585 (Apr. 1971).

Straffon et al., "Effects of Varying Concentrations of Formocresol of RNA Synthesis of Connective Tissues in Sponge Implants," 29 Oral Surgery, 915–25 (Jun. 1970).

Staffon et al., "The Effect of Formocresol on Hamster Connective Tissue Cells, A Histologic and Quantitative Radioautographic Study with Proline-$H^3$," 13 Archs Oral Biology, 271–89 (1968).

Publication entitled "Clinical Research Associates Newsletter," dated Aug. 1979, pp. 2–3.

Fischer, "Tissue Management for Making Impressions, Restorative Techniques for Individual Teeth," Chapter 15 (1981).

Advertisement appearing in Jul.–Aug. 1981 issue of Dental Products Reports offering the hemostatic agent "ASTRINGENT" and the Dento-Infusor applicator.

"Pulp Therapy", Chapter 9, pp. 187–208.

D. B. Kennedy, Chapters 15–17, "Principles of Pulp Therapy," Pediatric Operative Dentistry (1976).

R. E. McDonald, "Treatment of Deep Caries, Vital Pulp Exposure, and Pulpless Teeth in Children," Chapter 8, Dentistry for the Child and Adolescent (1969).

R. E. McDonald et al., "Treatment of Deep Caries, Vital Pulp Exposure, and Pulpless Teeth," pp. 157–160, 310–312, Dentistry for the Child and Adolescent (1978).

R. E. McDonald et al., "Treatment of Deep Carries, Vital Pulp Exposure, and Pulpless Teeth," pp. 218–222, 443–444, Dentistry for the Child and Adolescent (1983).

S. B. Finn et al., "Pulpal Treatment of Primary Teeth," pp. 226–234, Clinical Pedodontics, 3rd Ed. (1967).

Akbar, Ali, "A Five-Year Clinical Study of Formocresol Treatment in 120 Cases of pulpotomy in Permanent Molars," The Journal of Pedodontics, 242–46 (1987).

Ayers et al., "The Effect of Pulpotomies in Primary Molars on the Eruption of Succedaneous Teeth," The Journal of Pedodontics, 315–22 (1981).

Berger, J., "Pulp Tissue Reaction to Formo-Cresol and Zinc Oxide-Eugenol," Journal of Dentistry for Children, 13–28 (1965).

Emmerson et al., "Pulpal Changes Following Formocresol Applications on Rat Molars and Human Primary Teeth," 27 Journal of the Southern California States Dental Association, 309–323 (1959).

Fuks et al., "Clinical Evaluation of Diluted Formocresol Pulpotomies in Primary Teeth of School Children," Pediatric Dentistry, 321–324 (1981).

Garcia-Godoy, Franklin, "Direct Pulp Capping and Partial Pulpotomy with Diluted Formocresol in Primary Molars," Acta Odontol, Pediat., 57–61 (1984).

Judd et al., "Formocresol Concerns," Journal of the Canadian Dental Association, 401–04 (1987).

Kennedy et al., "Formocresol Pulpotomy in Teeth of Dogs with Induced Pulpal and PeriapicalPathosis," Journal of Dentistry for Children, 44–48 (1973).

Loos et al., "Biological Effects of Formocresol," Journal of Dentistry for Children, 29–33 (1973).

Massler et al., "Effects of Formo-Cresol on the Dental Pulp," Journal of Dentistry for Children, 277–79 (1959).

Morowa et al., "Clinical Evaluation of Pulpotomies Using DIlute Formocresol," Journal of Dentistry for Children, 28–31 (1975).

Mulder et al., "Consequences of Endodontic Treatment of Primary Teeth, Part II: A Clinical Investigation into the Influence of Formocresol Pulpotomy on the Permanent Successor," Journal of Dentistry for Children, 35–39 (1987).

Ranly, D., "Formocresol Toxicity, Current Knowledge," Acta Odontol. Pediat., 93–98 (1984).

Ranly, D., "Assessment of the Systemic Distribution and Toxicity of Formaldehyde Following Pulpotomy Treatment: Part I," Journal of Dentistry for Children, 431–34 (1985).

Ranly et al., "Assessment of the Systemic Distribution and Toxicity of Formaldehyde Following Pulpotomy Treatment: Part II," Journal of Dentistry for Children, 40–44 (1987).

Rolling et al., "A 3-Year Clinical Follow-Up Study of Pulpotomized Primary Molars Treated with the Formocresol Technique," Scand. J. Dent. Res.

Rolling et al., "Pulp Condition of Successfully Formo- (List continued on next page.)

OTHER PUBLICATIONS cresol-Treated Primary Molars," Scand. J. Dent. Res., 267-72 (1978).

Thomas et al., "Antibacterial Properties of Dilute Formocresol and Eugenol and Propylene Glycol," Oral Surg., 166-69 (1980).

Russo, Mary de Campos, "In Vivo Fixative Effect of Formocresol on Pulpotomized Deciduous Teeth of Dogs," Oral Surgery, 706-14 (1984).

Redit, D., "A Comparison and Evaluation of Two Formo-Cresol Pulpotomy Techniques Utilizing 'Buckley's Formo-Cresol," Journal of Dentistry for Children, 22-30 (1968).

Law et al., "Formocresol Pulpotomy in Deciduous Teeth," 69 The Journal of the American Dental Association, 73-79 (1964).

Garcia-Godoy et al., "Pulpal Resonse to Different Application Times of Formocresol," The Journal of Pedodontics, 176-193 (1982).

Berger, J. E., "A Review of the Erroneously Labeled 'Mummification' Techniques of Pulp Therapy," Oral Surgery, 131-44 (1972).

METHODS FOR PERFORMING VITAL DENTAL PULPOTOMY

BACKGROUND OF THE INVENTION

1. The Field of the Invention

This invention relates to methods for repairing teeth, and more particularly to such methods of tooth repair as involve partial amputation of the coronal pulp so that the vitality of the remaining pulp is maintained and the repaired tooth can function as a healthy biological unit.

2. The Background Art

When traumatic injury or the advancement of a carious lesion through the enamel and dentin of a tooth exposes the pulpal tissue to infection, various endodontic procedures may be appropriate to repair and preserve the tooth involved. In one of these, the vital dental pulpotomy, an effort is made to preserve healthy pulpal tissue in the pulp canals in the roots of the tooth.

In fully developed adult secondary teeth, such procedures are only occasionally undertaken. Instead, pulpal tissue is completely removed from the crown and root canals of the tooth and replaced by various materials in order to establish a seal to the canal openings at the root ends.

Nevertheless, many circumstances demand that all possible efforts be exercised in order to repair such teeth in a manner which retains at least a minimal amount of vitality therein. Typically, this will mean retaining the portion of the pulpal tissue in the pulp canals and replacing only the balance of that tissue with a suitable filling.

In the practice of dentistry for children, the conservation of the vitality and health of at least a portion of the dental pulp is a most important preventative health practice. No space-maintaining appliance can equal the natural primary tooth of the child during the development years. Neither can the psychological value of the retention of natural teeth be over estimated in developing the commitment of a child to its own dental hygiene.

In addition, primary teeth exhibit special structural characteristics which may make the full removal of pulpal tissue difficult in endodontic procedures. The root canals in such teeth tend to have cross sections that are more flat and ribbon-like than in adult teeth. This is particularly true as a primary tooth matures.

Root resorption in primary teeth requires that, if the pulpal tissue in root canals is removed, the filling used to replace that tissue, at least in the area of the roots of the teeth, must be capable of resorption with the rest of the root. This may undesirably limit the types of filling materials to which a practitioner may resort during dental repair.

Other circumstances also call for retention of vital pulpal tissue in the root canals of an injured or carious tooth. In young immature permanent teeth, the apical foramen may not have completely closed, thereby complicating any endodontic procedure in which removal of vital pulpal tissue from that portion of the tooth must be effected. In addition, select specific circumstances may even call for the vital dental pulpotomy in developed permanent teeth.

A vital dental pulpotomy involves the amputation of the vital coronal pulp down to the orifices of the pulp canals. This is usually accomplished by accessing the roof of the pulp chamber and using an excavator to remove the portion of the dental pulp desired. Frequently, bleeding in this stage of the procedure can be substantial and difficult to curtail, as the presence of a beginning infection in the pulpal tissue will normally stimulate blood flow thereto.

It is this increase in blood flow and the concomitant swelling that are the source of the pain which alerts a patient to seek dental help. Nevertheless, hemorrhaging must be arrested before further steps of the procedure can be undertaken. This is usually accomplished using dry cotton pellets or cotton pellets moistened with a hemostatic composition. The pellets are placed in the bottom of the excavated coronal pulpal chamber against the exposed ends of the pulpal tissue in the root canals. Other chemicals, such as formacresol, may be used; however, they are all too frequently not adequate to produce prompt hemostasis.

Once bleeding has been brought under control, a suitable drug is applied to the exposed cut ends of the pulpal tissue in order to inhibit bacterial activity at that site and in order to create thereat barrier regions of fixed pulpal tissue between the vital pulpal tissue in the pulp canals and the excavated coronal pulpal chamber. The barrier regions serve as buffers between the living tissue remaining and the filling placed in the coronal pulpal chamber in restoring the original tooth profile.

Unfortunately, several problems are inherent in such pulpotomy procedures. First, applying the hemostatic agent to the exposed cut ends of the pulpal material in the root canals is not always effective in bringing hemorrhaging under control rapidly enough to permit the complete restoration of the tooth in a single session with the patient. When hemorrhaging cannot be rapidly controlled, a two-stage pulpotomy is required. Initially, cotton pellets are sealed over the pulp stumps with a temporary filling, and thereafter the patient is forced to return for completion of the treatment some days later.

To an extent, the problem already described above is an inherent result of the fact that two distinct compounds, a hemostatic agent and a tissue fixing agent, must be applied in sequence to the ends of the cut pulpal tissues. The second application cannot occur until the hemostatic agent has been effective.

More significantly, however, the major drawback in prior methods of performing vital dental pulpotomies has been the character of the tissue-fixing compound applied to the cut ends of the pulpal tissue after hemorrhaging has been brought under control. It is necessary to fix the pulpal tissue at those sites in order to form between the vital pulpal tissue in the pulp canals and the material used to fill the coronal pulpal cavity a barrier that is bacteria-free, biocompatible, and stable. Prior to the present invention, the drug of choice for this purpose since the turn of the century has been formocresol—a mixture of formaldehyde and cresol. Unfortunately, formocresol is a known toxic, mutagenic, and carcinogenic material.

When employed in pulpotomies, formacresol causes undesirable local effects, as well as potential damage to liver and kidney tissues, which are remote from the treatment site. Among the harmful local effects noted are irritation of the tissues immediate to the treated tooth, abnormal levels of enamel defects in replacement permanent teeth, and rotation and displacement of those replacement teeth as they develop.

The literature has repeatedly called for the reevaluation of the use of formocresol in non-life threatening situations, such as pulpotomies. Examples of such literature are:

1. Loos et al., "An Enzyme Histochemical Study of the Effect of Various Concentrations of Formocresol on Connective Tissues," 31 *Oral Surgery* 571-85 (Apr. 1971).

2. Messer et al., "Long Term Effects of Primary Molar Pulpotomies on Succedaneous Bicuspids," 59 *Journal of Dental Research* 116-23 (Feb. 1980).

3. Meyers et al., "Tissue Change Induced by the Absorption of Formocresol from Pulpotomy Sites in Dogs," 5 *Pediatric Dentistry* 6-8 (1983).

4. Meyers et al., "Distribution of $^{14}$C-Formaldehyde After Pulpotomy with Formocresol," 96 *Journal of the American Dental Association* 805-13 (May 1978).

5. Lewis et al., "Formaldehyde in Dentistry: A Review of Mutagenic and Carcinogenic Potential," 103 *Journal of the American Dental Association* 429-34 (Sept. 1981).

6. Pashley et al., "Systemic Distribution of $^{14}$C-Formaldehyde From Formocresol-Treated Pulpotomy Sites," 59 *Journal of Dental Research* 602-7 (Mar. 1980).

7. Pruhs et al., "Relationship Between Formocresol Pulpotomies on Primary Teeth and Enamel Defects on their Permanent Successors," 94 *Journal of the American Dental Association* 698-700 (Apr. 1977).

8. Sipes et al., "The Use of Formocresol in Dentistry: A Review of the Literature," 17 *Quintessence International* 415-17 (1986).

9. Straffon et al., "Effect of Varying Concentrations of Formocresol on RNA Synthesis of Connective Tissue in Sponge Implants," 29 *Oral Surgery* 915-25 (June 1970).

Cumulatively, these and other studies have suggested that a search be undertaken to replace or reduce the use of formocresol in dental pulpotomies. Prior to the method of the present invention, such a replacement had not been located.

Thus, in relation to the performance of vital dental pulpotomies, a need exists to be able to promptly arrest hemorrhaging from the exposed cut ends of the pulpal tissue in the pulp canals so as to permit the subsequent steps of the pulpotomy procedure to be undertaken without delay. In this regard, it would be advantageous to be able to arrest hemorrhaging in situ in the pulpal tissue, rather than by a superficial application of a hemostatic agent thereto. In addition, a need exists to locate a composition with which to fix the exposed cut ends of such pulpal tissue after hemorrhaging has been arrested without introducing into the body a substance, such as formocresol, which causes deleterious effects on replacement teeth and local as well as remote body tissue. Finally, it would be highly advantageous to locate composition which could double both as a hemostatic and a tissue fixing agent when performing vital pulpotomies.

BRIEF SUMMARY AND OBJECTS OF THE INVENTION

The present invention involves methods for repairing a tooth comprising the initial steps of accessing the pulp chamber of the tooth and amputating the dental pulp in the pulp chamber to the orifices of the pulp canals. Thereafter, hemorrhaging is arrested from the exposed cut ends of the pulpal tissue in the pulp canals.

The exposed cut ends of the pulpal tissue then are fixed through the application of a composition containing ferric ions. Use of formocresol is avoided entirely.

The composition containing ferric ions preferably comprises an aqueous solution of ferric sulfate ($Fe_2(SO_4)_3$). In the alternative, ferric subsulfate ($Fe_4(OH)_2(SO_4)_5$) may be used.

The term "fixing," as used herein in relation to the exposed cut ends of pulpal tissue in the method of the present invention, refers to rendering that tissue less soluble, less changeable, and more resistant to the action of bacteria through a process which could generally be described as mummification. While the successful results from the use of the present invention are readily observable, the exact mechanism by which fixing of the exposed cut ends of the pulpal tissue occurs through the use of compositions containing ferric ions is not entirely understood.

As a result of the fixing of the exposed cut ends of the pulpal tissue, a barrier region is created of fixed tissue between the pulpal chamber and the vital pulpal tissue in the pulp canals. The tissue of the barrier region is preserved from infection and decomposition and serves as a buffer for the vital tissue that remains on the other side of the barrier in the pulp canals. Thereafter, the barrier regions of fixed tissue are themselves sealed from the pulpal chamber using a cement base, and the original profile of the tooth is restored by conventional techniques.

In one aspect of the present invention, both tissue fixation and the arresting of hemorrhaging from the exposed cut ends of the pulpal tissue is accomplished by administering compositions containing ferric ions. These compositions may be identical, in which case the two steps can be performed simultaneously. This results in simplification of the procedure and a corresponding savings in time.

Ferric sulfate or ferric subsulfate, when infused into the exposed cut ends of the pulpal tissue, operates promptly and efficiently to arrest hemorrhaging. The application of these compositions to the exposed ends of the pulpal tissue has also proven clinically effective in creating a barrier region of fixed tissue which permits the filling of the empty portion of the pulpal chamber and the restoration of the original tooth profile without reinfection or irritation to the living tissue in the pulp canals.

Advantageously, the ferric ion is common in the body chemistry. Accordingly, it is not toxic. Therefore, the use of a composition containing ferric ions in place of formocresol in such dental procedures accomplishes a major objective of the present invention: creation of a biocompatible barrier at the cut ends of the vital pulpal tissue retained in a tooth during a vital pulpotomy without introducing into the body a drug having toxic and carcinogenic qualities.

In addition, the present invention results in a streamlined method of performing vital pulpotomies, in that a single composition containing ferric ions will function simultaneously to control bleeding and to create a barrier region of fixed tissues as described above.

In yet another aspect of the present invention, the composition applied to the exposed cut ends of the pulpal tissue to control bleeding is infused into that tissue using a controlled diffusion medicament applicator. When a controlled diffusion medicament applicator is used to infuse a hemostatic composition into the exposed cut ends of the pulpal tissue in a vital pulpotomy, bleeding control is superior to that obtained by applying that composition using cotton pellets.

When cotton pellets are used, only a superficial application of the hemostatic composition results. Most of the coagulum formed is on the surface of the cut ends of the pulpal tissue and in the free blood in the evacuated coronal pulp chamber. Such coagulum must be washed away before the further step of fixing the tissue at the exposed cut ends of the pulpal tissue can occur. Washing away the coagulum, however, will frequently reinitiate bleeding.

According to one aspect of the method of the present invention, the hemostatic control material is not merely applied to the surface of the cut ends of the pulpal tissue, but infused directly into the openings of the capillaries therein under hydraulic pressure, producing hemostatis in the openings of the capillaries due to coagulation formation induced by the hemostatic control material.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

BRIEF DESCRIPTION OF THE DRAWINGS

In order that the manner in which the above-recited and other advantages and objects of the invention are obtained, a more particular description of the invention briefly described above will be rendered by reference to specific embodiments which are illustrated in the appended drawings. Understanding that these drawings depict only typical embodiments of the invention and are, therefore, not to be considered limiting of its scope, the invention will be described with additional specificity and detail through the use of the following drawings in which.

DESCRIPTION OF THE PREFERRED EMBODIMENT

Figure 1:
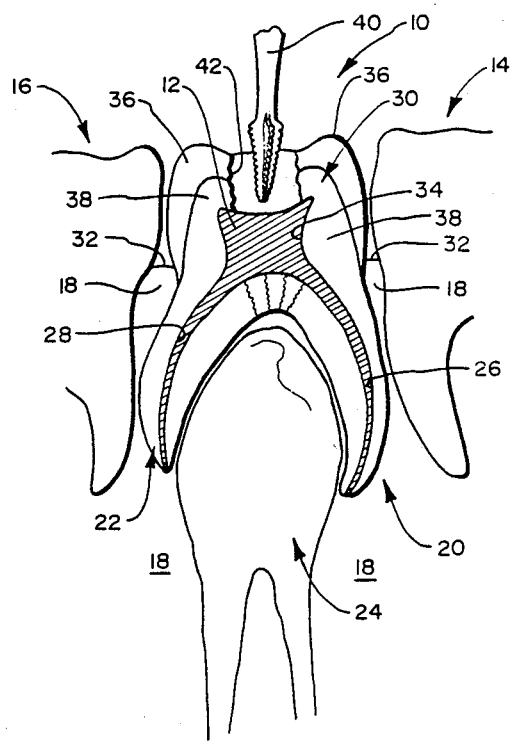
FIG. 1 is a cross-sectional view of a tooth to be repaired with a vital dental pulpotomy performed according to the method of the present invention and depicted in a first stage of that method.

Methods of the present invention for performing a vital pulpotomy will be illustrated in the sequence of drawings beginning with FIG. 1, which depicts a damaged tooth 10 in which traumatic injury or a carious invasion has exposed the pulp tissue 12 thereof to infection. Damaged tooth 10 is located between adjacent teeth 14 and 16 in gum tissue 18. The extent of the exposure of pulp tissue 12 to infection, in combination with the age and structural aspects of damaged tooth 10, render repair of damaged tooth 10 appropriate through the procedure of a vital pulpotomy.

While the method of the present invention is not exclusively limited to the repair of primary teeth, the use of vital pulpotomy procedures in such teeth is more common than in secondary teeth. Accordingly, damaged tooth 10 is shown in FIG. 1 as a primary tooth. The roots 20 and 22 of damaged tooth 10 nestle a growing secondary tooth bud 24 within gum tissue 18 below damaged tooth 10. Each root 20 and 22 of damaged tooth 10 contains a corresponding root or pulp canal 26 and 28, respectively, which is filled with pulp tissue 12.

It is the purpose of a vital pulpotomy in general, and of the methods of the present invention in particular, to repair damaged tooth 10 in such a manner as to arrest the spread of infection within pulp tissue 12, to restore the physical integrity of the crown 30 above gum line 22 which has permitted infection to enter pulp tissue 12, and to retain as a vital living component of the repaired tooth that portion of pulp tissue 12 housed in pulp canals 26 and 28.

Figure 2:
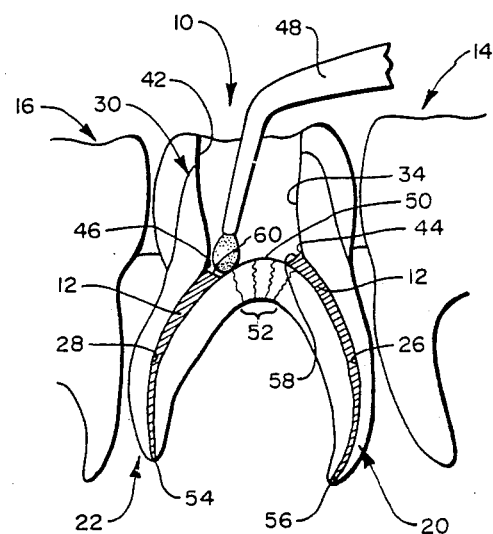
FIG. 2 is a cross-sectional view of the tooth of FIG. 1 shown in a second stage of the method of the present invention.

In the first stage of the preferred method of the present invention depicted in FIG. 1, damaged tooth 10 is anesthetized. The roof of coronal pulp chamber 34 is then accessed by the creation of an opening 42 through layers of enamel 36 and dentin 38 of crown 30 using, for example, a fissure bur 40. Opening 42 is widened to eliminate dentin overhangs 43 and afford unrestricted access to coronal pulp chamber 34, as is shown in FIG. 2.

In the second stage, dental pulp tissue 12 in coronal pulp chamber 34 is amputated to the orifices 44 and 46 of pulp canals 26 and 28, respectively, using a round bur or curette 48, for example. While the walls of coronal pulp chamber 34 must be scoured clean of dental pulp tissue, care must be taken to avoid perforating floor 50 of coronal pulp chamber 34 in the process.

Floor 50 of a coronal pulp chamber is understood to be permeated by minute accessory channels 52 which afford for the transport of some of the nutrients required by the dental pulp tissue in the coronal pulp chamber. The removal of all dental pulp tissue 12 from coronal pulp chamber 34 obviates the utility of accessory channels 52. Nevertheless, the portion of dental pulp tissue 12 remaining in pulp canals 26 and 28 following the step of removing dental pulp tissue 12 from coronal pulp chamber 34 will continue to receive nutrients through apical foramen 54 and 56 at the tips of roots 20 and 22, respectively.

Figure 3A:
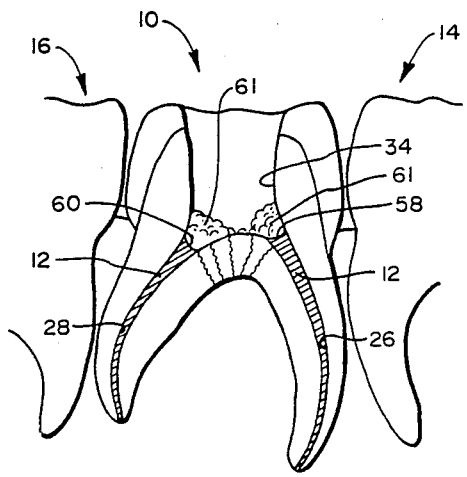
FIG. 3A is a cross-sectional view of the tooth of FIG. 1 shown in a third stage of the method of the present invention.
Figure 3B:
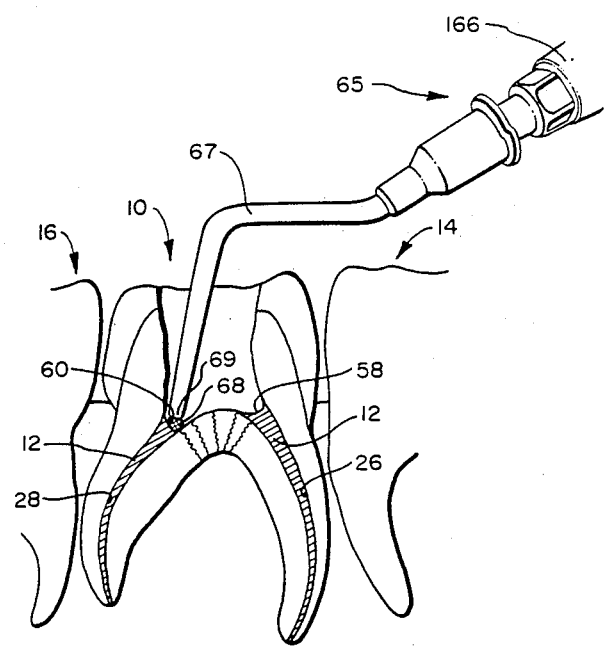
FIG. 3B is a cross-sectional view of the tooth of FIG. 1 shown in an alternate third stage of the method of the present invention.

FIGS. 3A and 3B show alternative third stages of the method of the present invention in which hemorrhaging is arrested from the exposed cut ends 58 and 60 of the remaining dental pulp tissue 12 and in which exposed cut ends 58 and 60 are fixed to create at orifices 44 and 46, respectively, barrier regions of fixed tissue.

In FIG. 3A, this is shown as accomplished by the application of dry cotton pellets 61 to exposed cut ends 58 and 60. Alternatively, cotton pellets 61 may be moistened with epinephrine, or with a composition containing ferric ions, such as ferric sulfate or ferric subsulfate.

For most procedures, a ferric sulfate concentration in the range of from about 4% to about 30%, or more preferably from about 10% to about 20% is acceptable. As an example, a 15.5% aqueous solution of ferric sulfate has been found to serve adequately in this regard. A suitable commercially available form of ferric sulfate at this level of concentration is sold under the trademark Astringedente ® from Ultradent Products, Inc. Ferric subsulfate at the standard concentration found in Monsel Solution of from about 19% to 20%, or at concentrations in the range from about 3% to about 40%, are equally satisfactory for this purpose.

Figure 4:
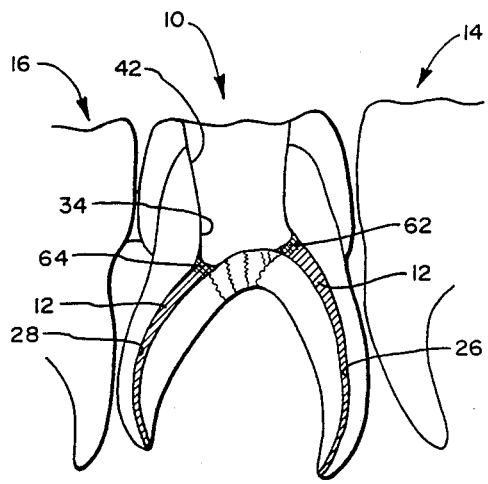
FIG. 4 is a cross-sectional view of the tooth of FIG. 1 shown in a fourth stage of the method of the present invention.

In the present invention, if dry or moistened cotton pellets 61 are used to arrest hemorrhaging from the exposed cut ends 58 and 60 of pulpal tissue 12, hemorrhaging must be completely stopped before the succeeding step is attempted. When hemorrhaging has been arrested, the exposed cut ends 58 and 60 of dental pulp tissue 12 remaining in pulp canals 26 and 28, respectively, are fixed by applying thereto a composition containing ferric ions. As shown in FIG. 4, an objective of such a procedure is to create barrier regions 62 and 64 between orifices 46 and 48 of corresponding pulp canals 26 and 28 and the tissue of exposed cut ends 58 and 60, respectively.

As indicated above, the term "fixing," as used herein in the method of the present invention in relation to the exposed cut ends of pulpal tissue, such as exposed cut ends 58 and 60, means to render that tissue less soluble, less changable, and more resistant to the action of bacteria. The process in which this is accomplished can generally be likened to mummification or leatherfication. The barrier regions resulting have proven to function as a clinically adequate bacteria static barriers, as well as buffers preventing irritation to the dental pulp tissue 12 remaining in pulp canals 26 and 28.

Where cotton pellets 61 carrying a composition containing ferric ions are used to arrest hemorrhaging from the exposed cut ends 58 and 60 of dental pulp tissue 12, no additional step of drug application is required in the method of the present invention in order to fix exposed ends 58 and 60 to create therefrom barrier regions 62 and 64, respectively. This advantageously reduces the number of procedures required to effect a successful vital dental pulpotomy.

As shown in FIG. 3B, an appropriate composition may be applied to expose cut ends 58 and 60 of dental pulp tissue 12 other than through the use of cotton pellets. Instead, a controlled diffusion medicament applicator 65 may advantageously be used. Devices such as medicament applicator 65 include a reservoir 66 for holding a quantity of hemostatic agent and a generally tubular shaped member 67 communicating with reservoir 66 through which the hemostatic agent in reservoir 66 can be applied directly to a site in a controlled manner. This is accomplished through the application of hydraulic pressure to the hemostatic agent in reservoir 66 by operation of a plunger (not shown) fitted thereinto. A porous material 68 is secured substantially filling distal end 69 of tubular member 67 so that the hemostatic agent dispensed from medicament applicator 65 exits tubular member 66 under hydraulic pressure.

In use, porous material 68 at distal end 69 of tubular member 67 is placed against exposed cut ends 58 and 60 of dental pulp tissue 12. Then syringe-type operation of the plunger fitted in reservoir 66 infuses the hemostatic into the openings of the capillaries of the live tissue of exposed cut ends 58 and 60. This results in hemostatis occurring in the orifices of the capillaries, rather than on the surface, of exposed cut ends 58 and 60.

In this manner, prompt and efficient in situ control of hemorrhaging from exposed cut ends 58 and 60 can be effected. Furthermore, if the composition applied for arresting hemorrhaging is the same as that used to fix exposed cut ends 58 and 60, a single step simultaneously creates barrier regions 62 and 64 of fixed dental pulp tissue 12.

Once the procedures described in relation to either FIG. 3A or FIG. 3B have been completed, the result will be a damaged tooth 10 as shown in FIG. 4 having a coronal pulp chamber 34 emptied of dental pulp tissue, but pulp canals 26 and 28 continuing to be filled therewith. The tissue at exposed cut ends 58 and 60 of dental pulp tissue 12 remaining in pulp canals 26 and 28, respectively, will have ceased to hemorrhage and have been fixed into barrier region 62 and 64, respectively.

In contrast to the prior art practice of using formocresol in the process of fixing such tissue, the method of the present invention introduces no such toxic, carcinogenic material into the body of a patient, either temporarily or on an extended basis as a continuing source of infusion. The body chemistry routinely processes ferric ions. Accordingly, the use of a composition containing ferric ions, such as ferric sulfate or ferric subsulfate, as either or both a hemorrhage control composition or a tissue-fixing composition, represents a dramatic increase in safety to the patient.

Figure 5A:
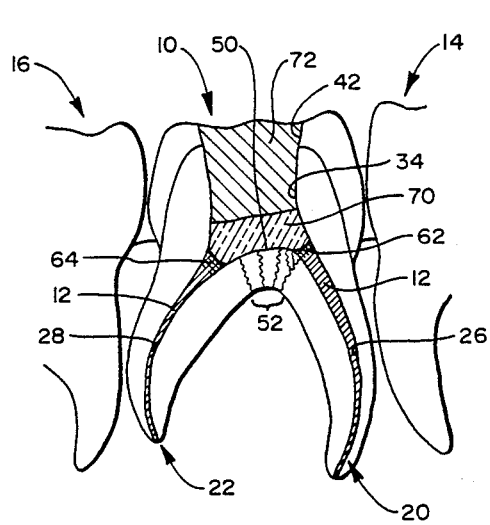
FIG. 5A is a cross-sectional of the tooth of FIG. 1 shown in a fifth and final stage of the method of the present invention.
Figure 5B:
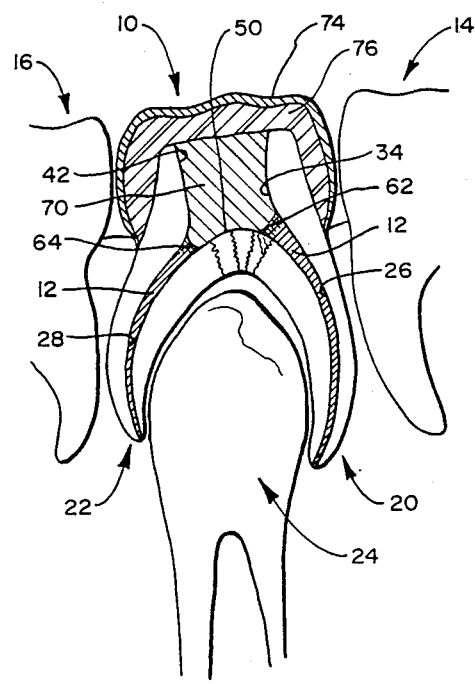
FIG. 5B is the tooth of FIG. 1 of an alternate final and fifth stage of the method of the present invention.

Once proper fixing of the tissue at exposed cut ends 58 and 60 has been accomplished, the original profile of damaged tooth 10 is restored. In general, this will involve the sealing of barrier region 62 and 64 and accessory channels 52 from coronal pulp chamber 34 using a cement base. This is followed by filling of tooth 10 with a suitable amalgum and optionally with a capping procedure. As shown in FIGS. 5A and 5B, this concluding stage to the repair of damaged tooth 10 can take several suitable forms.

In FIG. 5A, a cement base layer 70 has been applied above barrier regions 62 and 64 and on floor 50 of coronal pulp chamber 34 as a seal. Cement base layer 70 may be comprised of a mixture of eugenol and zinc oxide. Above cement base layer 70, coronal pulp chamber 34 and opening 42 thereinto has been filled by an amalgam 72 or other adequate restorative material in order to recreate the original profile of damaged tooth 10.

Cement base layer 70 is understood to perform two functions. First, cement base layer 70 serves to prevent mercury commonly included in an amalgam, such as amalgum 72, from diffusing into the body of the patient through contact with vital tissue. Secondly, because it contains the phenol eugenol, cement base layer 70 is believed to serve as a bacterial static barrier enhancing the effectiveness of barrier regions 62 and 64.

Alternatively, as shown in FIG. 5B, damaged tooth 10 can be restored to its original profile by preparing a crown 74 duplicating that profile and then capping tooth 10 with the crown. In such a case, damaged tooth 10 will generally be entirely filled with the material comprising cement base 70 in FIG. 5A, and then crown 74 will be adhered thereto using some form of cement 76, such as a zinc phosphate cement. In children, crown 74 will frequently be composed of stainless steel, as such teeth will often fracture after pulpotomies due to brittleness arising from dentin dehydration.

In either case, whether the method depicted in FIG. 5A or that shown in FIG. 5B is used to restore the original profile of damaged tooth 10, after repair that tooth is able to function as a healthy biological unit with vital pulpal tissue 12 continuing to be housed in pulp canals 26 and 28. If damaged tooth 10 is a primary tooth, then resorption of roots 20 and 22 can occur in a normal fashion, permitting the emergence of a successor tooth from tooth bud 24 beneath damaged tooth 10.

Further, because the method of the present invention eliminates all use of formocresol, that replacement tooth can be expected to exhibit no unusual number of enamel defects and no abnormal disorientation due to the pulpotomy procedure employed to save damaged tooth 10. Damaged tooth 10 will accordingly serve as an effective spacer between adjacent teeth 14 and 16 to preserve room for its replacement secondary tooth.

Thus, it can be seen that the method of the present invention is a method for repairing teeth so that the vitality of some of the pulp tissue is maintained. The repaired tooth can accordingly be retained in location for its normal lifetime until replaced by a secondary tooth or lost due to other causes not related to the condition of the pulp tissue. This procedure permits normal root resorption to facilitate the growth and emergence of secondary teeth.

The use of a composition containing ferric ions in place of formocresol permits the creation of biocompatible barriers at the cut ends of the vital pulp tissue retained in the tooth, without introducing into the body chemicals having known toxic and carcinogenic qualities.

In addition, the present invention results in a method of performing vital pulpotomies which is simplified by comparison with those previously employed. A single composition may be used in the method of the present invention both to control bleeding and to fix tissue at the barrier regions.

If a controlled diffusion medicament applicator is used, that composition may be infused into the exposed ends of the pulpal tissue, rather than applied superficially, resulting in even more efficient and effective hemostasis and tissue fixation.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for repairing a tooth comprising the steps of:
   (a) accessing the pulp chamber of the tooth;
   (b) amputating the dental pulp in the pulp chamber to the orifices of the pulp canals;
   (c) arresting hemorrhaging from the exposed cut ends of the pulpal tissue in the pulp canals;
   (d) fixing the exposed cut ends of the pulpal tissue by applying thereto a composition containing ferric ions to create barrier regions of fixed tissue between the pulp chamber and vital pulpal tissue in the pulp canals; and
   (e) sealing the barrier regions of fixed tissue from the pulp chamber using a cement base.

2. A method for repairing a tooth as recited in claim 1, wherein said step of arresting hemorrhaging is accomplished by administering a composition containing ferric ions to the exposed cut ends of the pulpal tissue.

3. A method for repairing a tooth as recited in claim 2, wherein the composition containing ferric ions administered to the exposed cut ends of the pulpal tissue in said step of arresting hemorrhaging comprises ferric sulfate.

4. A method for repairing a tooth as recited in claim 3, wherein the composition containing ferric ions administered to the exposed cut ends of the pulpal tissue in said step of arresting hemorrhaging comprises an aqueous solution of ferric sulfate having a concentration in the range from about 4 percent to about 30 percent.

5. A method for repairing a tooth as recited in claim 4, wherein the aqueous solution of ferric sulfate has a concentration in the range from about 10 percent to about 20 percent.

6. A method for repairing a tooth as recited in claim 5, wherein the aqueous solution of ferric sulfate has a concentration of about 15 percent.

7. A method for repairing a tooth as recited in claim 2, wherein the composition containing ferric ions administered to the exposed cut ends of the pulpal tissue in said step of arresting hemorrhaging comprises a composition containing ferric subsulfate.

8. A method for repairing a tooth as recited in claim 7, wherein the composition containing ferric subsulfate has a concentration in the range from about 19 percent to about 20 percent.

9. A method for repairing a tooth as recited in claim 2, wherein the composition containing ferric ions administered to the exposed cut ends of the pulpal tissue in said step of arresting hemorrhaging is infused into the exposed cut ends of the pulpal tissue by using a medicament applicator.

10. A method for repairing a tooth as recited in claim 9, wherein the composition containing ferric ions is infused into the exposed cut ends of the pulpal tissue using the steps of:
    (a) introducing the composition containing ferric ions into a medicament applicator capable of controlled dispensing of the composition containing ferric ions by hydraulic pressure through a porous surface of the medicament applicator;
    (b) placing the porous surface of the medicament applicator against the exposed cut ends of the pulpal tissue; and
    (c) infusing the composition containing ferric ions under pressure into the openings of the capillaries of the live exposed cut ends of the pulpal tissue such that fixing of the exposed cut ends of the pulpal tissue occurs in the orifices of the capillaries thereof.

11. A method for repairing a tooth as recited in claim 1, wherein the composition containing ferric ions applied to the exposed cut ends of the pulpal tissue in said step of fixing comprises ferric sulfate.

12. A method for repairing a tooth as recited in claim 11, wherein the composition containing ferric ions applied to the exposed cut ends of said pulpal tissue in said step of fixing comprises an aqueous solution of ferric sulfate.

13. A method for repairing a tooth as recited in claim 12, wherein the aqueous solution of ferric sulfate has a concentration in the range from about 4 percent to about 30 percent.

14. A method for repairing a tooth as recited in claim 13, wherein the aqueous solution of ferric sulfate has a concentration in the range from about 10 percent to about 20 percent.

15. A method for repairing a tooth as recited in claim 14, wherein the aqueous solution of ferric sulfate has a concentration of about 15 percent.

16. A method for repairing a tooth as recited in claim 1, wherein the composition containing ferric ions applied to the exposed cut ends of the pulpal tissue in said step of fixing comprises a composition containing ferric subsulfate.

17. A method for repairing a tooth as recited in claim 16, wherein the composition containing ferric sulfate has a concentration in the range from about 19 percent to about 20 percent.

18. A method for repairing a tooth as recited in claim 1, wherein the cement base comprises a mixture of eugenol and zinc oxide.

19. A method for repairing a tooth as recited in claim 18, further comprising the step of restoring the original profile of the tooth.

20. A method for repairing a tooth as recited in claim 19, wherein said step of restoring the original profile of the tooth comprises the step of filling the tooth to the original profile thereof with an amalgam.

21. A method for repairing a tooth as recited in claim 19, wherein said step of restoring the original profile of the tooth comprises the steps of preparing a crown substantially duplicating the original profile of the tooth and capping the tooth with the crown.

22. A method for repairing a tooth as recited in claim 1, wherein the composition containing ferric ions applied to the exposed cut ends of the pulpal tissue in said step of fixing is infused into the exposed cut ends of the pulpal tissue by using a medicament applicator.

23. A method for repairing a tooth as recited in claim 22, wherein the composition containing ferric ions is infused into the exposed ends of the pulpal tissue using the steps of:
(a) introducing the composition containing ferric ions into a medicament applicator capable of controlled dispensing of the composition containing ferric ions by hydraulic pressure through a porous surface of the medicament applicator;
(b) placing the porous surface of the medicament applicator against the exposed cut ends of the pulpal tissue; and
(c) infusing the composition containing ferric ions under pressure into the exposed cut ends of the pulpal tissue to fix the exposed cut ends of the pulpal tissue without the use of formocresol.

24. A method for repairing a tooth as recited in claim 1, wherein the method is used to restore primary teeth.

25. In a vital pulpotomy, wherein a composition is applied to an exposed cut end portion of the vital pulpal tissue to create from the exposed cut end portion of the vital pulpal tissue a barrier region of fixed tissue for contact with a cement base installed thereafter, the composition including ferric ions.

26. In a vital pulpotomy as recited in claim 25, the composition comprised an aqueous solution of ferric sulfate.

27. In a vital pulpotomy as recited in claim 26, the composition comprised an aqueous solution of ferric sulfate having a concentration in the range from about 4 percent to about 30 percent.

28. In a vital pulpotomy as recited in claim 27, the composition comprises an aqueous solution of ferric sulfate having a concentration in the range from about 10 percent to about 20 percent.

29. In a vital pulpotomy as recited in claim 28, the composition comprises an aqueous solution of ferric sulfate in a concentration or about 15 percent.

30. In a vital pulpotomy as recited in claim 25, the composition comprises a composition containing ferric subsulfate.

31. In a vital pulpotomy as recited in claim 30, the composition comprises a composition containing ferric subsulfate in a concentration in the range from about 3 percent to about 40 percent.

32. In a vital pulpotomy as recited in claim 31, the composition comprises a composition containing ferric subsulfate in a concentration in the range from about 19 percent to about 20 percent.

33. A method for repairing a tooth comprising the steps of:
(a) accessing the pulp chamber of the tooth;
(b) amputating the dental pulp in the pulp chamber to the orifices of the pulp canals;
(c) arresting hemorrhaging from the exposed cut ends of the pulpal tissue in the pulp canals;
(d) fixing the exposed cut ends of the pulpal tissue to create therefrom barrier regions of fixed tissue between the pulp chamber and vital pulpal tissue in the pulp canals by applying a composition containing ferric ions to the exposed cut ends of the pulpal tissue;
(e) sealing the barrier regions of fixed tissue from the pulp chamber using a cement base; and
(f) restoring the original profile of the tooth.

34. A method for repairing a tooth as recited in claim 33, wherein the composition containing ferric ions comprises ferric sulfate.

35. A method for repairing a tooth as recited in claim 33, wherein the composition containing ferric ions comprises an aqueous solution of ferric sulfate.

36. A method for repairing a tooth as recited in claim 35, wherein the aqueous solution of ferric sulfate has a concentration in the range from about 4 percent to about 30 percent 37. A method for repairing a tooth as recited in claim 36, wherein the aqueous solution of ferric sulfate has a concentration in the range from about 10 percent to about 20 percent.

38. A method for repairing a tooth as recited in claim 37, wherein the aqueous solution of ferric sulfate has a concentration of about 15 percent.

39. A method for repairing a tooth as recited in claim 33, wherein the composition containing ferric ions comprises a composition containing ferric subsulfate.

40. A method for repairing a tooth as recited in claim 39, the composition comprises a composition containing ferric subsulfate in a concentration in the range from about 3 percent to about 40 percent.

41. A method for repairing a tooth as recited in claim 40, wherein the composition containing ferric subsulfate has a concentration in the range from about 19 percent to about 20 percent.

42. A method for repairing a tooth as recited in claim 33, wherein the composition containing ferric ions is infused into the exposed cut ends of the pulpal tissue by using a medicament applicator.

43. A method for repairing a tooth as recited in claim 42, wherein the composition containing ferric ions is infused into the exposed ends of the pulpal tissue using the steps of:
(a) introducing the composition containing ferric ions into a medicament applicator capable of controlled dispensing of the composition containing ferric ions by hydraulic pressure through a porous surface of the medicament applicator;

(b) placing the porous surface of the medicament applicator against the exposed cut ends of the pulpal tissue; and (c) infusing the composition containing ferric ions under pressure into the live exposed cut ends of the pulpal tissue and the openings of the capillaries therein to produce hemostasis in said openings of said capillaries due to coagulation formation induced by said composition and to fix the exposed cut ends of the pulpal tissue.

44. A method for repairing a tooth as recited in claim 33, wherein the cement base comprises a mixture of eugenol and zinc oxide.

45. A method for repairing a tooth as recited in claim 33, wherein said step of restoring the original profile of said tooth comprises the step of filling the tooth to the original profile thereof with an amalgam.

46. A method for repairing a tooth as recited in claim 33, wherein said step of restoring the original profile of the tooth comprises the steps of preparing a crown substantially replicating the original profile of the tooth and capping the tooth with the crown.

47. A method for performing a vital pulpotomy in primary teeth comprising the steps of:
(a) accessing the pulp chamber of the tooth;
(b) amputating the dental pulp in the pulp chamber to the orifices of the pulp canals;
(c) arresting hemorrhaging from the exposed cut ends of the pulpal tissue in the pulp canals;
(d) in the absence of formocresol, fixing the exposed cut ends of the pulpal tissue to create therefrom barrier regions of fixed tissue between the pulp chamber and vital pulpal tissue in the pulp canals by infusing into the tissue of the exposed cut ends an aqueous solution of ferric sulfate having a concentration in the range from about 4 percent to about 30 percent using a medicament applicator;
(e) sealing the barrier regions of fixed tissue from the pulp chamber using a mixture of eugenol and zinc oxide; and
(f) restoring the original profile of the tooth.

48. A method for performing a vital pulpotomy in primary teeth as recited in claim 47, wherein the composition containing ferric ions comprises an aqueous solution of ferric sulfate having a concentration of about 15 percent.

49. A method for repairing a tooth as recited in claim 47, wherein the composition containing ferric ions is infused into the exposed ends of the pulpal tissue using the steps of:
(a) introducing the composition containing ferric ions into a medicament applicator capable of controlled dispensing of the composition containing ferric ions by hydraulic pressure through a porous surface of the medicament applicator;
(b) placing the porous surface of the medicament applicator against the exposed cut ends of the pulpal tissue; and
(c) infusing the composition containing ferric ions under pressure into the openings of the capillaries of the live exposed cut ends of the pulpal tissue such that fixing of the exposed cut ends of the pulpal tissue occurs in the orifices of the capillaries thereof.

50. A method for performing a vital pulpotomy in primary teeth as recited in claim 47, wherein said step of restoring the original profile of the tooth comprises filling the tooth to the original profile thereof with an amalgam.

51. A method for performing a vital pulpotomy in primary teeth as recited in claim 47, wherein said step of restoring the original profile of the tooth comprises the steps of preparing a crown substantially replicating the original profile of the tooth and capping said tooth with the crown.

* * * * *

UNITED STATES PATENT AND TRADEMARK OFFICE
CERTIFICATE OF CORRECTION

PATENT NO. : 4,895,517

DATED : January 23, 1990

INVENTOR(S) : Dan E. Fischer

It is certified that error appears in the above-identified patent and that said Letters Patent is hereby corrected as shown below:

Column 1, lines 37-38, "development years." should be --developmental years.--
Column 1, line 39, "over estimated" should be --overestimated--
Column 1, line 40, "its own dental hygiene" should be --his or her own dental hygiene--
Column 12, line 49, "comprises" should be --comprising--

Signed and Sealed this

Thirteenth Day of August, 1991

Attest:

HARRY F. MANBECK, JR.

*Attesting Officer*          *Commissioner of Patents and Trademarks*